United States Patent
Itoh et al.

(10) Patent No.: US 6,913,591 B2
(45) Date of Patent: Jul. 5, 2005

(54) PERSONAL INJECTOR FOR LIQUID MEDICINE

(75) Inventors: Takehito Itoh, Osaka (JP); Susumu Kobayashi, Osaka (JP); Hideyuki Tomita, Osaka (JP)

(73) Assignee: Nipro Corporation, Osaka-fu (JP)

( * ) Notice: Subject to any disclaimer, the term of this patent is extended or adjusted under 35 U.S.C. 154(b) by 336 days.

(21) Appl. No.: 10/095,713

(22) Filed: Mar. 13, 2002

(65) Prior Publication Data

US 2002/0133114 A1 Sep. 19, 2002

(30) Foreign Application Priority Data

Mar. 15, 2001 (JP) .................................. 2001-073883

(51) Int. Cl.[7] .................................................. A61M 31/00
(52) U.S. Cl. ............................................................ 604/67
(58) Field of Search .................... 128/DIG. 1, DIG. 12, 128/DIG. 13; 222/327, 386; 604/207, 208, 156, 232, 67

(56) References Cited

U.S. PATENT DOCUMENTS

| 4,950,246 A | * | 8/1990 | Muller | ................ 128/DIG. 1 |
| 5,593,390 A | * | 1/1997 | Castellano et al. | ......... 604/207 |
| 5,662,612 A | * | 9/1997 | Niehoff | ....................... 604/155 |
| 5,690,618 A | | 11/1997 | Smith et al. | ........... 128/DIG. 1 |
| 5,928,201 A | | 7/1999 | Poulsen et al. | ........ 128/DIG. 1 |
| 6,004,285 A | * | 12/1999 | Sugahara | ...................... 604/67 |

FOREIGN PATENT DOCUMENTS

| EP | 0 293 958 A1 | 7/1988 |
| EP | 0 362 484 A2 | 11/1990 |

\* cited by examiner

*Primary Examiner*—Manuel Mendez
(74) *Attorney, Agent, or Firm*—Birch, Stewart, Kolasch & Birch, LLP (57) ABSTRACT

Personal injector for liquid medicine comprises a housing provided with needle-mounting part, medicine container holder and connecting port to a personal computer; plunger arranged in housing; electric motor for driving plunger; limit switch for limiting the forward movement of plunger; starting point sensor for detecting return of plunger to the starting point; and substrate having display and mode-select switch mounted thereon. The plunger is movable between the starting point and forward limit point. Limit switch is arranged at the forward limit point. When limit switch is turned on, motor drives plunger in reverse to move it to the starting point thereof.

19 Claims, 8 Drawing Sheets

PERSONAL INJECTOR FOR LIQUID MEDICINE

BACKGROUND OF THE INVENTION

The present invention relates to a personal injector for liquid medicine. More particularly, the invention relates to a simplified injector for liquid medicine, which is intended for patients who have chronic diseases and require self-administration of liquid medicines, and which enables the user to administer a dose of liquid medicine with ease in safety as well as to perform automatic injection and control of the administration.

Conventionally, pen-type liquid drug injectors have been used for administration of liquid medicines, for example, insulin to diabetic patients. Such a drug injector generally comprises a body provided with a dosage-setting dial, an injection button, a piston and unit-setting indicator; a medicine container holder and a cap. In use, the administration of insulin is carried out by a method comprising the steps of inserting a cartridge into a medicine container holder of the body, fitting a needle on a tip of the body, injecting the liquid medicine for air-release and confirmation of fluid communication, and setting a dosage of the liquid medicine.

However, the liquid medicine injectors of the conventional pen-type have the following disadvantages: When the cartridge has been emptied, the user may have the false impression that the injector got out of order. The injection of the setting dosage can not be confirmed since the injection of the liquid medicine is carried out only while the injection button is pushed. The given dose can not be quantified accurately since the liquid medicine may drip down when the needle is accidentally taken out from the skin during administration. The correct control of administration can not be performed since the residual liquid medicine content is not expressed numerically.

BRIEF SUMMARY OF THE INVENTION

The present invention has been made under such circumstances to provide a personal injector for liquid medicine, which makes it possible to automatically and simply perform injection and medication control.

Another object of the present invention is to provide a personal injector for liquid medicine, which makes it possible to administer a dose of liquid medicine with ease in safety.

To this end, the personal injector for liquid medicine of the present invention is so designed as to be connected to a computer, provided with a limit switch for stopping the forward movement of a push member or a plunger at a forward limit point, wherein the plunger is adapted to be returned to its starting point by reverse drive of a electric motor when the limit switch is turned on.

According to the present invention, there is provided a personal injector for liquid medicine comprising:
a housing having a distal end and a proximal end and including a needle-mounting part, a medicine container holder, and a connecting port to a computer;
a plunger arranged in said housing and adapted to be longitudinally moved by said motor between a starting point and a forward limit point within the housing;
an electric motor for driving said plunger;
a limit switch arranged at the forward limit point to stop the forward movement of said plunger;
a starting point sensor for detecting return of the plunger to the starting point; and
a substrate arranged in said housing and provided with a display and mode-select switch; and
wherein said plunger is adapted to be moved to the starting point by reverse driving of the motor when said limit switch is turned on.

In case that the desired dosage is greater than a residual liquid medicine content of the cartridge, and operation mode is set to non-additional dosage mode, the limit switch may be adapted to be turned on. In case that the desired dosage is greater than the residual liquid medicine content, and that operation mode is set to an additional dosage mode, the motor may drive the plunger until it reaches to the forward limit point where the limit switch is turned on and a difference between the desired dosage and the actually injected amount of the liquid medicine may be calculated to set it as an additional desired dosage as well as to display it on the display.

Preferably, the personal injector may be provided with means for detecting a clogging of a needle attached to the needle-mounting part. The housing may be provided with a battery holder for holding a battery to use the battery as a power source. Alternatively, the housing may be provided with a connector adapted to be connected to an external power source. When using the battery, the housing is preferably provided with a power switch. Preferably, the plunger is provided with a manual dial so that the plunger is manually moved in case of battery shutoff, electric power failure or trouble in the circuit. The medicine container holder may be provided with a cartridge detect switch for detecting presence of the cartridge.

In order to prevent wrong operation, the housing may be provided with a confirmation switch adjacent to the mode select switch for confirmation of the selected operation mode and the starting point sensor being "on". The housing may be provided with an alarm which is activated when the needle clogging is detected or when the plunger is returned to the starting point, and which is deactivated when the confirmation switch is pushed.

The present invention will become more fully understood from the detailed description given hereinbelow and the accompanying drawings, which are given by way of illustration only, and thus are not limitative of the present invention.

DETAILED DESCRIPTION OF THE INVENTION

As illustrated in FIGS. 1 to 4, a personal injector for liquid medicine comprising a housing 1 provided with a needle-mounting part 11, a medicine container holder 12 and a connecting port 13 to a personal computer not illustrated in the drawings; a plunger 2 arranged in the housing 1; an electric motor 3 arranged in the housing for driving the plunger 2; a limit switch 4 for limiting the forward movement of the plunger 2; a starting point sensor 5 for detecting return of the plunger 2 to the starting point; and a substrate 6 provided with a display 61 and a operation mode-select switch 62. The plunger 2 is movable between a starting point and a forward limit point.

Figure 3:
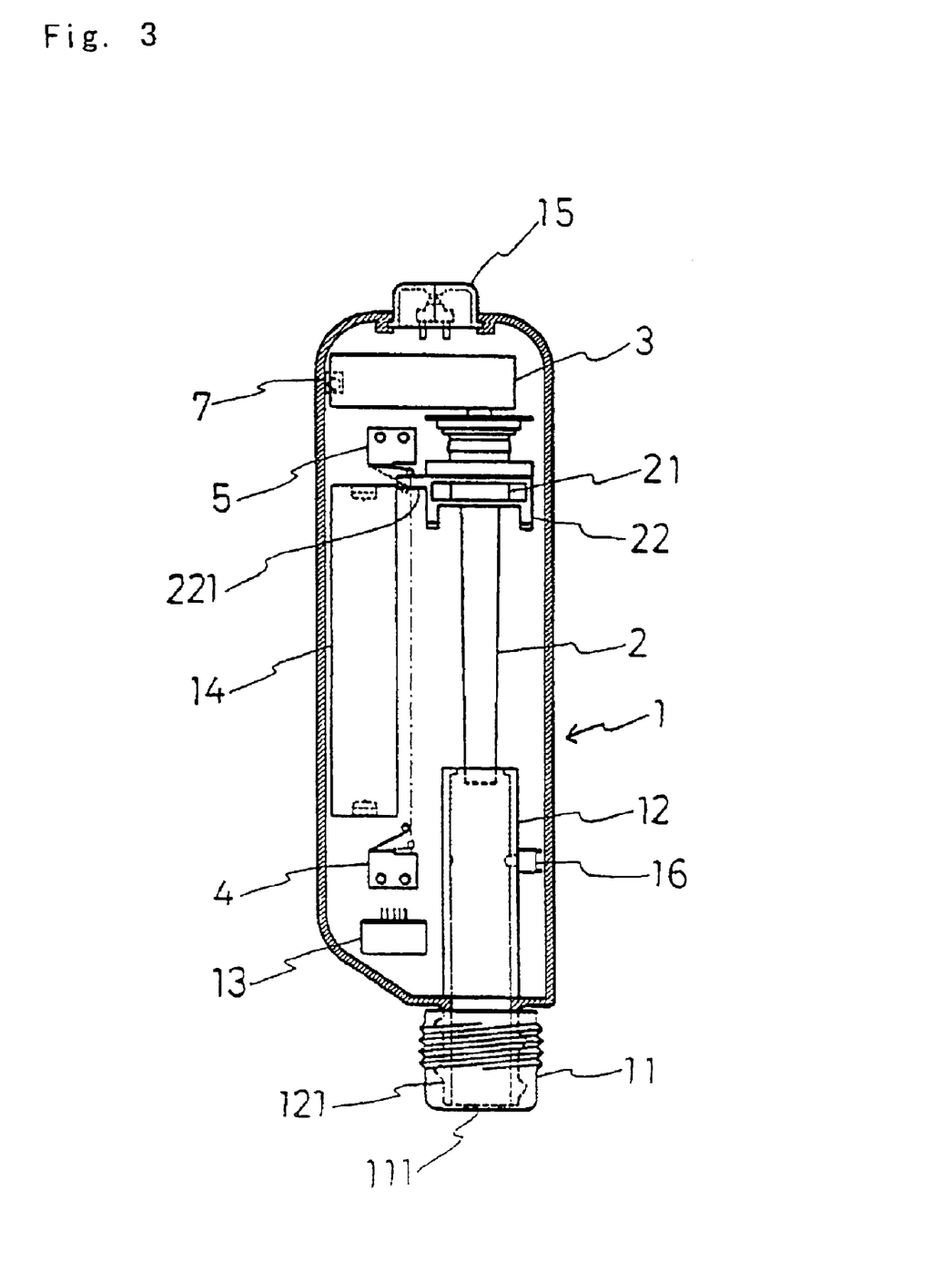
FIG. 3 is a schematic illustration of an internal structure of the injector shown in FIG. 1.
Figure 4:
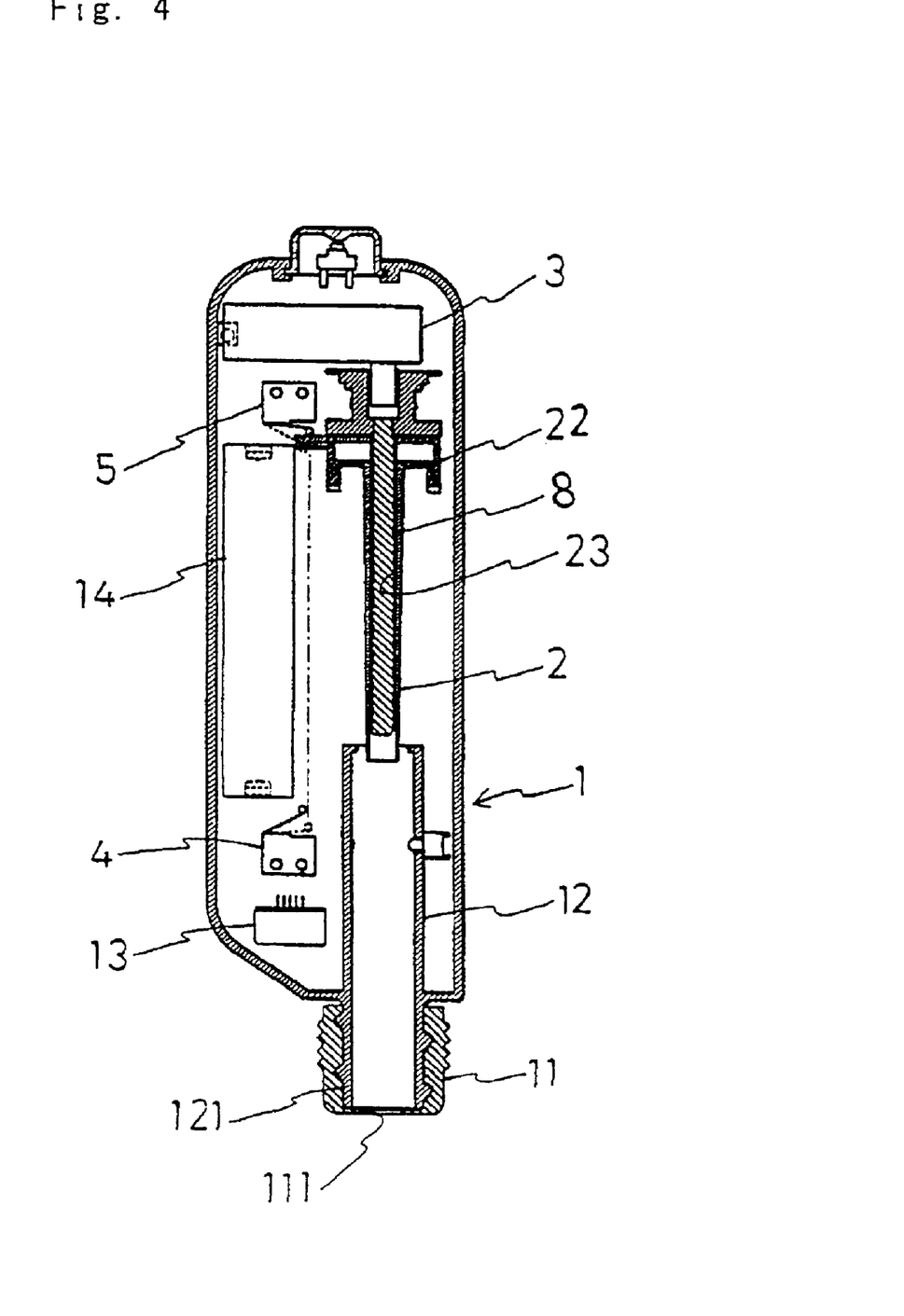
FIG. 4 is a schematic illustration of an internal structure of the injector shown in FIG. 1.

The limit switch is arranged at the forward limit point of the plunger 2. If the limit switch 4 is turned on, the motor 3 drives the plunger 2 in the reverse direction to move it to the starting point thereof.

The housing 1 is a box-shaped member having a distal end and a proximal end and is provided at the distal end thereof with the needle-mounting part 11. The housing 1 is further provided with the connecting port 13 to a personal computer at a suitable position thereof. The electric motor 3 is arranged in the housing 1 and serves as means for driving the plunger 2. The medicine container holder 12 is arranged in the housing 1 adjacent to the needle mounting part 11 and on the distal side thereof. The plunger 2 is movably arranged in the housing 1 on the distal side of the medicine container holder 12. The needle (not shown) attached to the needle mounting part 11, medicine container holder 12 and plunger 2 are arranged on the same longitudinal axis. Numeral 131 designates a cap for connector port to the personal computer, 141 is a cover for battery case, 17 is a cover to be opened or closed when operating the movable dial, 18 is a support used for placing the injector on a desk or optional place.

In the embodiment illustrated in FIGS. 1–4, a cartridge (not illustrated) is inserted into the medicine container holder 12 through the distal end of the housing 1. However, it may be set in the medicine container holder 12 by opening a cover of the housing 1. In case of that the injector is of a type wherein a cartridge (one form of a cartridge) is inserted into the medicine container holder from the distal end, the medicine container holder 12 is formed in the form of a hollow cylinder and partially protruded from the distal end of the housing 1, as illustrated in FIGS. 1–4.

The needle-mounting part 11 is a cap-like member with a through-hole 111 at a top plane thereof and is removably fitted on a protruded portion 121 of the medicine container holder 12 in the proper way such as, for example, screw engagement. When installing the cartridge 12 into the injector, the needle-mounting part 11 is removed first from the protruded portion 121 of the medicine container holder 12 and screwed again on the protruded portion 121 after inserting the cartridge into the medicine container holder 12. Thus, the needle-mounting part 11 pushes the cartridge in the medicine container holder 12 at a top plate thereof. This means that the needle-mounting part 11 provides a function of positioning the cartridge since the cartridge is pushed by a top plate of the needle-mounting part. The through-hole 111 may take any desired size, provided that it is smaller than the- diameter of the cartridge but sufficiently greater than an outer diameter of a canula of the needle.

In order to improve the portability, the housing 1 may be provided with a battery holder 14 as illustrated in FIGS. 3 and 4 to use a battery as a power source for the injector. However, the housing 1 may be provided with an external power receptacle (not shown) to use the external power source as the power source. Further, the housing 1 may be provided with both battery holder 14 and the external power receptacle to use then selectively. When the injector is so designed as to use any battery, it is preferred to provide a power switch 15 at the proximal end of the housing 1 to save power consumption.

The plunger 2 is a hollow cylindrical member having an internal thread 23 and a flanged portion 22 provided at the proximal end thereof. On the proximal end of the flanged portion 22, there is provided a protrusion 221 protruded radially from the flanged portion 22 so as to come into contact with the starting point sensor 5 and limit switch 4. The plunger 2 is screw-mounted on a ball screw 8 and adapted to be driven by the motor 3. By activating the motor 3, a rotatory motion thereof is converted into the rotatory motion of the ball screw 8, which is then converted into a longitudinal linear motion of the plunger 2 engaged at the internal thread 23 thereof with the ball screw 8. Thus, the plunger 2 is moved forward or backward along the longitudinal axis of the ball screw 8. The proximal end 22 of the plunger 2 may be provided with a manual dial 21 to allow the user to manually drive the plunger 2 in case of unexpected situations such as battery shutoff, electric power failure or trouble in the circuit.

The plunger 2 is driven by the motor 3 from the starting point where the protrusion 221 comes into contact with the starting point sensor 5 to the forward limit point where the protrusion 221 comes into contact with the limit switch 4, or vice versa. When the limit switch 4 is turned on, the motor 3 drives the ball screw 8 in the reverse direction until the plunger 2 is returned back to the starting point. The limit switch 4 is positioned at the forward limit point for the plunger 2 and turned on when the protrusion 221 comes into contact therewith or when a desired dosage is greater than the residual liquid medicine content in the cartridge and the operation mode has been set to a non-additional dosage mode.

The starting point sensor 5 is positioned at the starting point and turned on to stop the backward movement of the plunger 2 when the plunger 2 is returned to the starting point and comes into contact with the starting point sensor 5 at the protrusion 221 thereof. A micro switch or a software switch generally constitutes the limit switch 4. It is preferred to use a micro switch and a software switch together. A micro switch generally constitutes the starting point sensor 5.

Preferably, the injector is provided with means for detecting any clogging of the needle attached to the needle-mounting part 11, to avoid any trouble of the motor 3 resulting from the clogging of the needle. Means for detecting any clogging of the needle comprises a strain gauge 7 arranged between the motor 3 and the housing 1 to detect a small strain occurred in the motor 3. Another means for detecting any clogging of the needle comprises means for detecting the revolution of the motor or a moving velocity of the plunger 2. In this case, the clogging of the needle is detected by comparing a normal value of the revolution of the motor or a moving velocity of the plunger 2 to an actual revolution or moving velocity measured during operation of the injector. If the actual value is lower than the normal value, the needle is determined as being clogged up. Another means for detecting any clogging of the needle comprises a load cell attached to the plunger 2 to detect a stress from the plunger 2. In this case, the needle is determined as being clogged up when the stress exceeds a certain set value. The term "needle" used herein includes needles having a tube, such as winged catheters.

If the plunger 2 is positioned at the starting point, turning on the power switch 15 activates the motor 3 even when the cartridge is not held in the medicine container holder 12. In order to avoid such erroneous behavior, it is preferred to provide a mean for detecting presence of the medicine container in the medicine container holder 12. To this end, the medicine container holder 12 is provided with a container-detecting switch 16 which is turned on by setting the medicine container in the medicine container holder 12 to allow the motor 3 to be activated only when the cartridge is set correctly in the medicine container holder 12.

Figure 1:
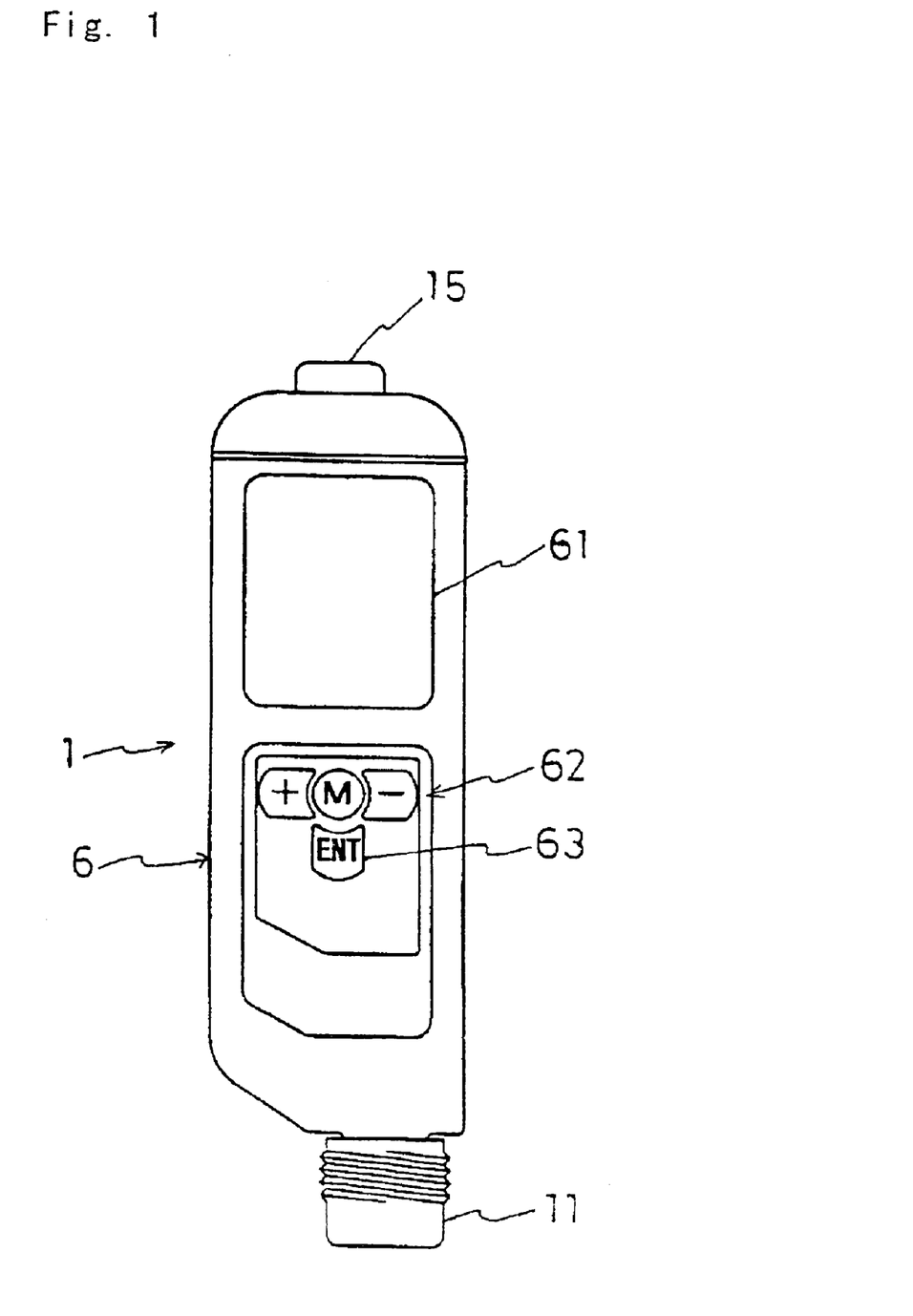
FIG. 1 is a plan view of a personal injector for liquid medicine according to the present invention.
Figure 2:
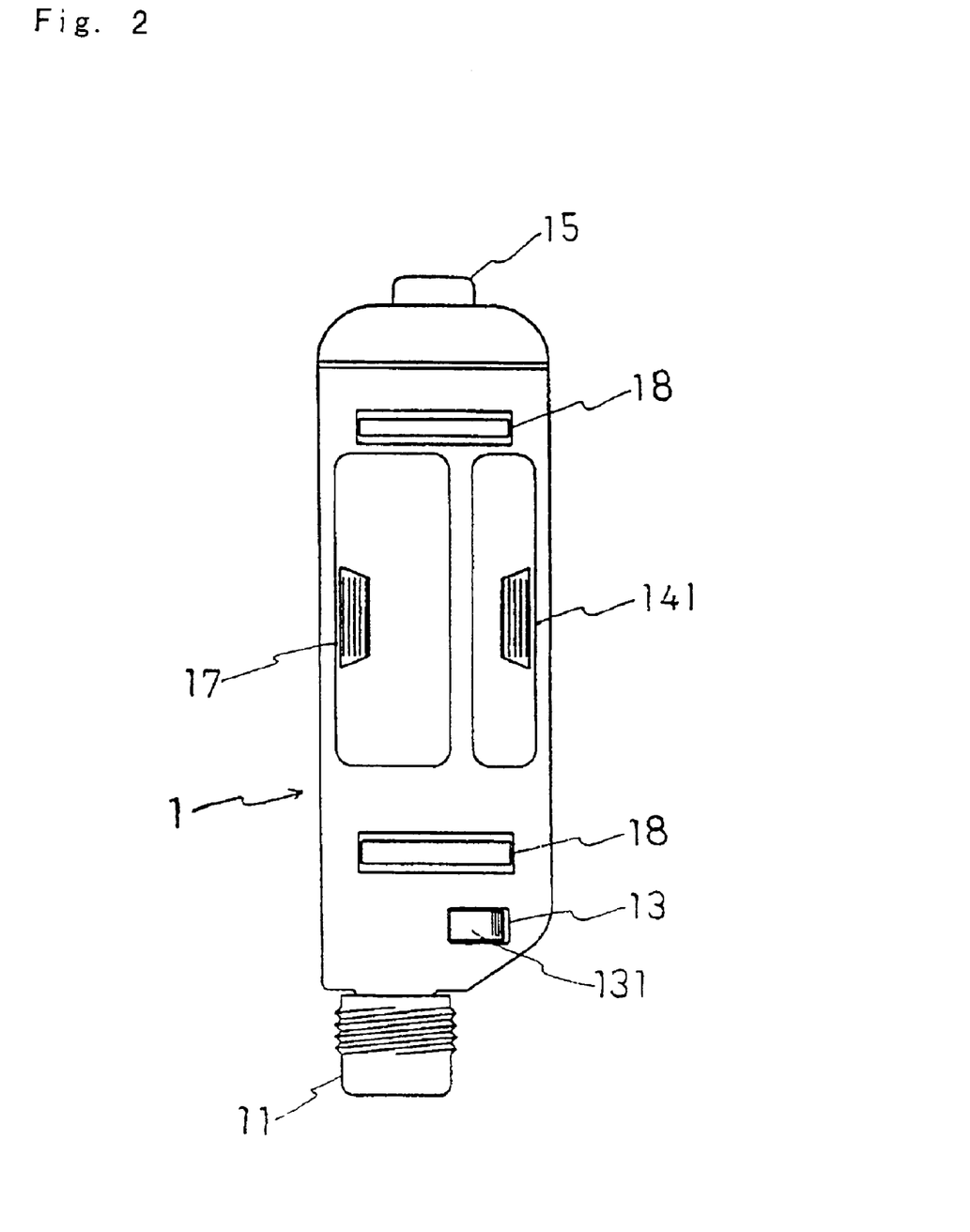
FIG. 2 is a bottom view thereof.

The substrate 6 has a display 61, a mode-select switch 62 and a control unit (not shown) mounted thereon. The mode select switch 62 is adapted to allow the user to set a desired dosage, medication records, the kind of alarm (sounds, flashing caution signal, etc.), loudness level or length of sound (when the alarm is set to sound), need for additional dosage and the like. The display 61 is adapted to display the time for next administration, a residual volume of liquid medicine, an additional dosage and other necessary information in addition to the operation mode set by the mode-select switch 62. The information or data except for those set by the mode select switch 62 are input by a personal computer electrically connected to the injector through the connecting port 13. As the display 61, it is preferred to use a liquid crystal display. The substrate 6 may be provided with a confirmation switch 63 adjacent to the mode select switch 62 to confirm on-state of the starting point sensor, set mode of the injector, notice of administration and the like. This enables to prevent erroneous use of the injector. The housing 1 may be provided with an alarm (not shown) which is activated at the time of detection of the clogging of the needle, or at the time of return to the stating point of the plunger 2, and deactivated by pushing the confirmation switch 63. The alarm may be constituted by one element selected from the group consisting of light emitting diodes for flashing caution signal, buzzers and chimes. The injector may be provided with all of these alarms to allow the user to optionally select one or more of these elements.

The control system for the injector of the present invention will be explained below with reference to the accompanying drawings.

Figure 5:
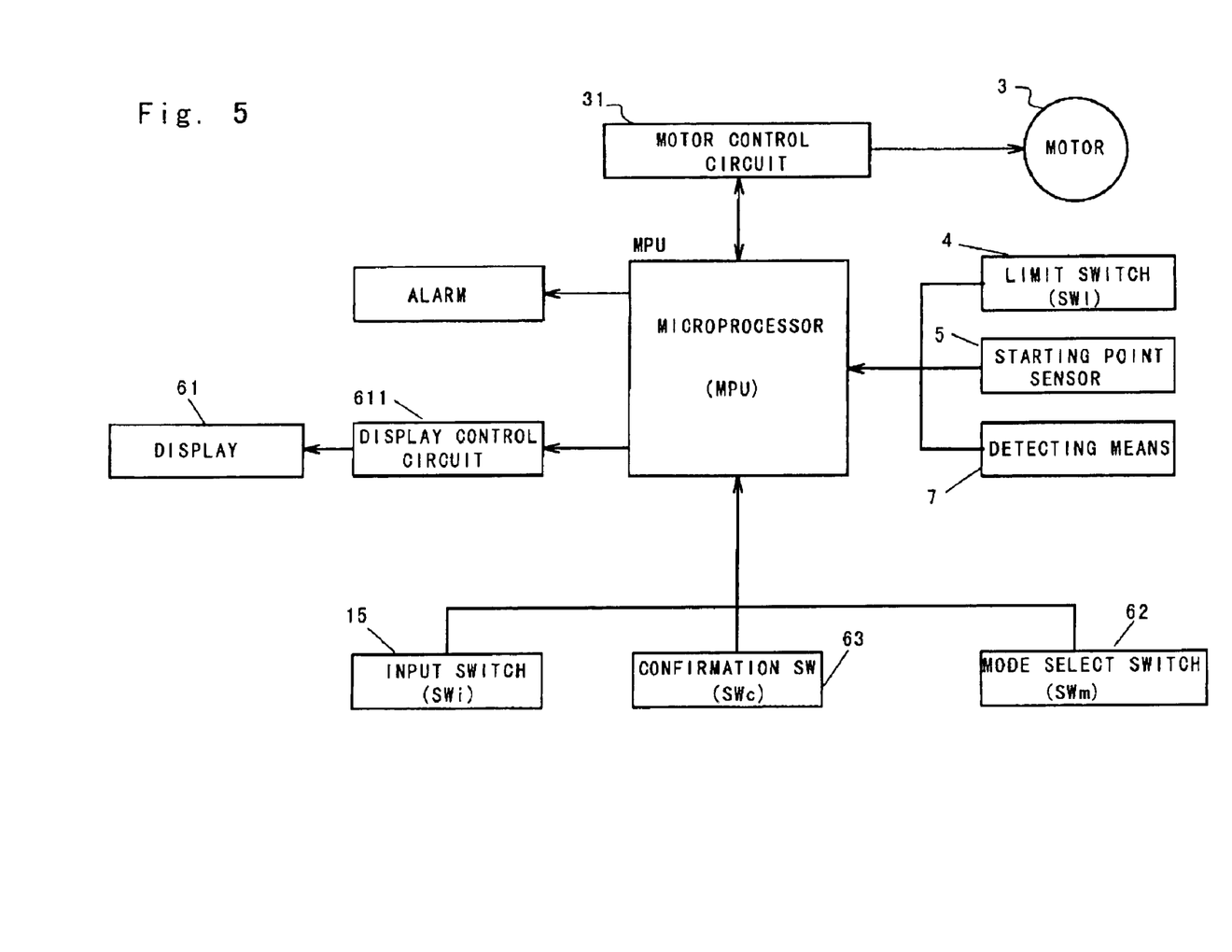
FIG. 5 is a schematic block diagram of the injector according to the present invention.

As illustrated in FIG. 5, the control system includes a microprocessor (MPU) adapted to control the alarm (ALM), display 61 through a display control circuit 611 and motor 3 through a motor control circuit 31. The microprocessor MPU is adapted to receive and process information sent from the power switch 15, confirmatory information sent from the confirmation switch 63, mode select information sent from mode select switch 62, information sent from the limit switch 4 and starting point sensor 5, information sent from the clogging-detect means 7, and control information sent from the motor control circuit. The additional amount of the medicine is calculated by MPU, determined and displayed as a difference between a desired dosage and an actual dosage of the medicine.

Figure 6:
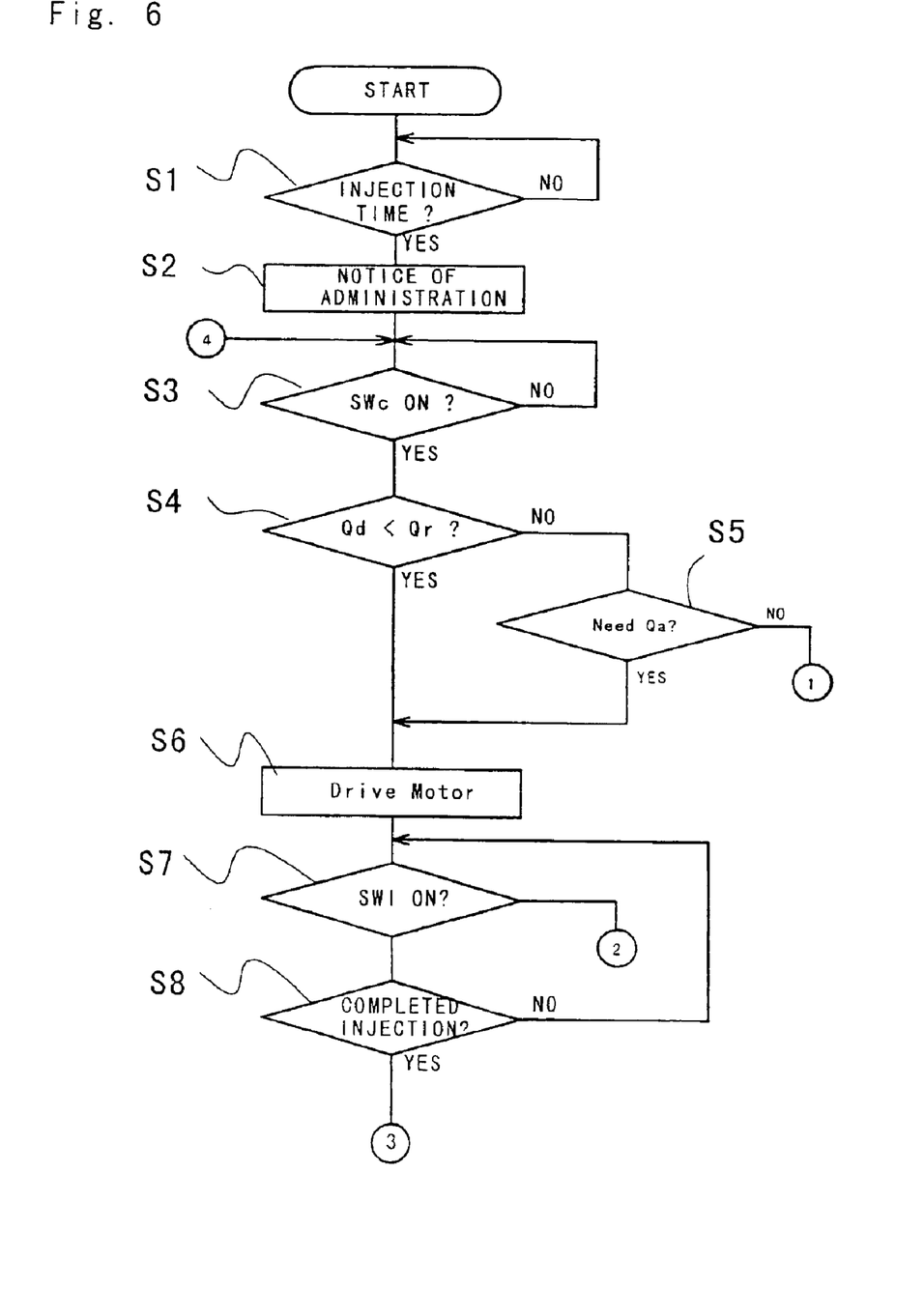
FIG. 6 is a flow chart showing operation of the injector according to the present invention.
Figure 7:
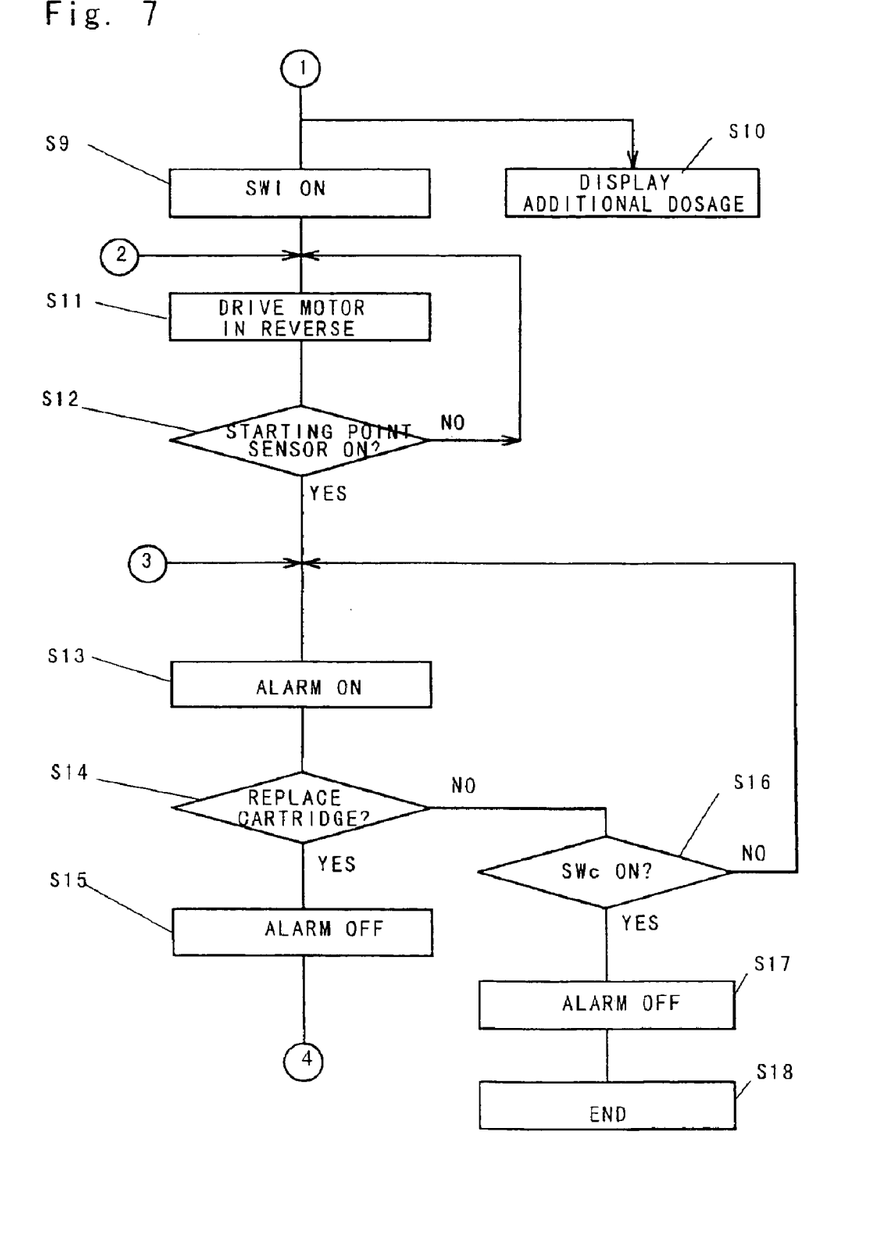
FIG. 7 is a flow chart showing operation of the injector according to the present invention.
Figure 8:
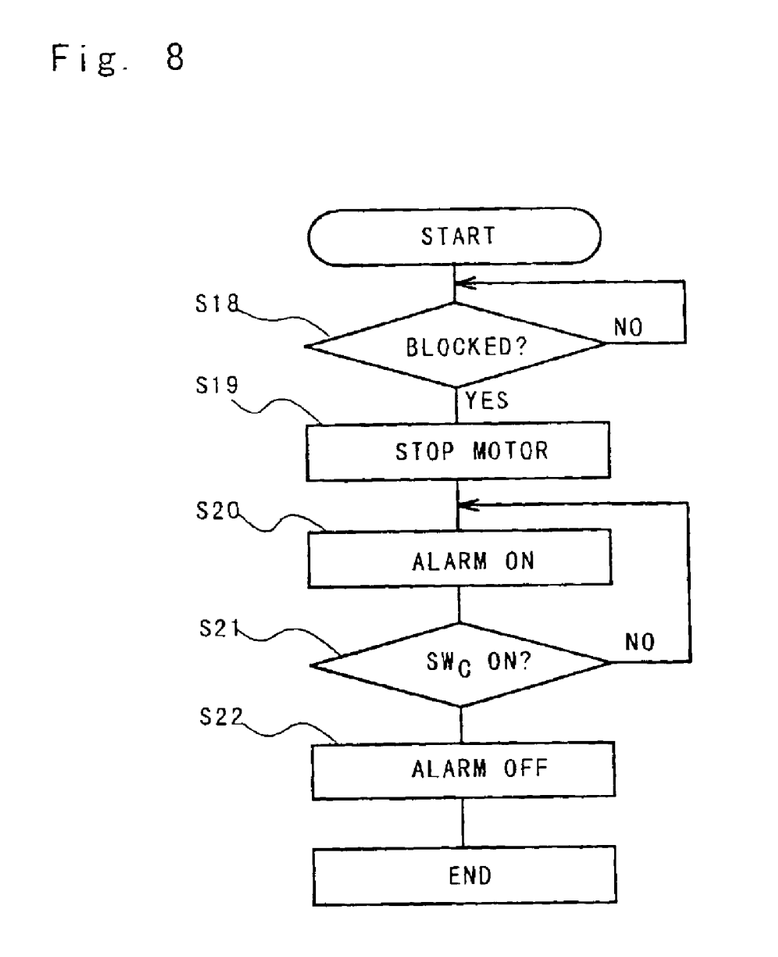
FIG. 8 is a flow chart showing operation for detection of a needle clogging.

When turning on the power switch 15, the control system is activated and is ready to accept an information, as illustrated in FIG. 6. If the actual time is reached to a set time for administration (step 1), the microprocessor MPU gives notice to the user by alarm and, if necessary, displays message on the screen of the display 61 (step 2). The notice of administration is held for a certain period, for example, 5 to 10 seconds. By pushing the confirmation switch 63 (step 3), the MPU displays relationship between a desired dosage and a residual liquid medicine content of the cartridge. If the desired dosage is equal to or smaller than the residual content (step 4), the motor 3 is activated to perform injection of the medicine (step 6). After completing injection of the desired dosage of the medicine (step 8), the operation of MPU varies with the conditions of the injector. If the desired dosage is judged at step 4 as being smaller than the residual content, MPU activates the alarm (step 13) as illustrated in FIG. 7. By pushing the confirmation switch 63, the MPU stops the alarm (step 17) and terminates the operation for administration of the liquid medicine.

On the other hand, if the desired dosage is judged at step 4 as being equal to the residual content, the plunger 2 reaches to the forward limit point and turns on the limit switch 4 (step 9), whereby completing the administration of the desired dosage of the liquid medicine. Simultaneously therewith, the MPU displays an additional dosage on the screen of the display 61 as being zero (step 10) and activates the motor 3 in reverse (step 11). Thus, the plunger 2 is moved backward and returned to the starting point. When the plunger 2 has reached to the starting point, the starting point sensor 5 is turned on by the plunger 2 (step 12) and the alarm is activated by MPU (step 13). By replacing the consumed cartridge with new one (step 14) or pushing the confirmation switch 63 (step 16), the alarm is stopped (step 15 or step 17), thereby completing the operation of administration.

If the desired dosage is judged as being greater than the residual content (step 4), the user is requested to push a mode switch (M) of the mode select switch 62 to display an additional dosage mode on the screen of the display 61. At this point, it is sufficient for the user to push either a plus-signed switch (+) in case of the additional dosage being required or a minus-signed switch (−) in case of no additional dosage being required (step 5). By pushing the plus-signed switch, the motor 3 is activated to start administration of the liquid medicine. During the administration of the liquid medicine, the plunger 2 reaches the forward limit point and turns on the limit switch 4 (step 7). Simultaneously therewith, the MPU displays the additional dosage on the screen of the display 61 as illustrated in FIG. 7 and activates the motor 4 in reverse (step 11). Thus, the plunger 2 is moved backward and returned to the starting point. When the plunger 2 reaches the starting point, the starting point sensor 5 is turned on (step 12) and the alarm is activated by MPU (step 13). By replacing the consumed cartridge with new one (step 14), the alarm is stopped (step 15). By pushing the confirmation switch 63 (step 3), the administration of additional dosage is started in the same manner as mentioned above for the case where the desired dosage is judged as being smaller than the residual content.

If the minus-signed switch is pushed (step 5), the limit switch 4 is turned on (step 9) and the motor 4 is driven in reverse (step 11), as illustrated in FIG. 7. Thus, the plunger 2 is moved backward and returned to the starting point. At this point, the starting point sensor 5 is turned on (step 12) and the alarm is activated by MPU (step 13). By replacing the consumed cartridge with new one (step 14), the alarm is stopped (step 15). By pushing the confirmation switch 63 (step 3), the administration of the desired dosage is started in the same manner as mentioned above for the case where the desired dosage is judged as being smaller than the residual content.

As will be understood from the above, the personal injector of the present invention makes it possible to automatically and simply perform injection and medication control. Further, the personal injector of the present invention makes it possible to administer a dose of liquid medicine with ease in safety by provision of clogging-detect means and the manual operating dial.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A personal injector for liquid medicine comprising:
   a housing having a distal end and a proximal end and including a needle-mounting part, a medicine container holder, and a connecting port to a computer;
   a plunger arranged in said housing and adapted to be longitudinally moved between a starting point and a forward limit point within the housing;
   an electric motor for driving said plunger;
   a limit switch arranged at the forward limit point to stop the forward movement of said plunger;
   a starting point sensor for detecting return of the plunger to the starting point; and
   a substrate arranged in said housing and provided with a display, a mode-select switch, and a confirmation switch;
   wherein the confirmation switch confirms an on-state of the starting point sensor, a set mode of the injector, and a notice of an administration of the liquid medicine, and
   wherein said plunger is adapted to be moved to the starting point by the reverse driving of the motor when said limit switch is turned on.

2. The personal injector according to claim 1, wherein said limit switch is turned on when a desired dosage is greater than a residual liquid medicine content.

3. The personal injector according to claim 1,
   wherein said motor is driven to move the plunger to a forward limit point where the limit switch is turned on, in case that a desired dosage is greater than a residual liquid medicine content and an operation mode is set to an additional dosage mode, thereby calculating and displaying a difference between the desired dosage of the liquid medicine and an actual dosage of the liquid medicine to determine an additional desired dosage.

4. The personal injector according to claim 1, wherein said injector is adapted to detect clogging of a needle attached to the needle-mounting part.

5. The personal injector according to claim 1, wherein said housing is provided with a battery holder for holding a battery and with a power switch.

6. The personal injector according to claim 1, wherein said housing is provided with a connector for a power source.

7. The personal injector according to claim 1, wherein said plunger is provided with a manual dial which allows the user to manually move the plunger forward.

8. The personal injector according to claim 1, wherein said medicine container holder is provided with a medicine container detect switch for detecting presence of the medicine container.

9. The personal injector according to claim 1, wherein a rotary motion of the electric motor is converted into a rotary motion of a ball screw, which is then converted into a longitudinal linear motion of the plunger.

10. The personal injector according to claim 1, wherein the electric motor is adapted to cause the plunger move in either a forward or a backward longitudinal linear motion.

11. The personal injector according to claim 4, further comprising a strain gauge arranged between the electric motor and the housing.

12. The personal injector according to claim 1, wherein the mode select switch includes a mode switch M for displaying an additional dosage mode on the display when a desired dosage is judged to be greater than a residual content of the liquid medicine, a plus-signed switch for a user to push in case the additional dosage is required, and a minus-signed switch for the user to push in case the additional dosage is not required.

13. The personal injector according to claim 12, wherein pushing the push-signed switch activates the motor to start the administration of the liquid medicine.

14. The personal injector according to claim 12, wherein pushing the minus-signed switch turns on the limit switch, and drives the motor in reverse.

15. A personal injector for liquid medicine comprising:
   a housing having a distal end and a proximal end and including a needle-mounting part, a medicine container holder, and a connecting port to a computer;
   a plunger arranged in said housing and adapted to be longitudinally moved between a starting point and a forward limit point within the housing;
   an electric motor for driving said plunger;
   a limit switch arranged at the forward limit point to stop the forward movement of said plunger;
   a starting point sensor for detecting return of the plunger to the starting point; and
   a substrate arranged in said housing and provided with a display and a mode-select switch;
   wherein the mode select switch includes a mode switch M for displaying an additional dosage mode on the display when a desired dosage is judged to be greater than a residual content of the liquid medicine, and
   wherein said plunger is adapted to be moved to the starting point by the reverse driving of the motor when said limit switch is turned on.

16. The personal injector according to claim 15, the mode select switch further comprises a plus-signed switch for a user to push in case the additional dosage is required, and a minus-signed switch for the user to push in case the additional dosage is not required.

17. The personal injector according to claim 16, wherein pushing the push-signed switch activates the motor to start the administration of the liquid medicine.

18. The personal injector according to claim 16, wherein pushing the minus-signed switch turns on the limit switch, and drives the motor in reverse.

19. The personal injector according to claim 15, the substrate being provided with a confirmation switch for confirming an on-state of the starting point sensor, a set mode of the injector, and a notice of an administration of the liquid medicine.

* * * * *